(12) United States Patent
Leeton

(10) Patent No.: US 9,329,106 B2
(45) Date of Patent: May 3, 2016

(54) METHODS, APPARATUSES AND KITS FOR COLLECTING CHEMICAL SAMPLES

(71) Applicant: UOP LLC, Des Plaines, IL (US)

(72) Inventor: Eric Leeton, Corpus Christi, TX (US)

(73) Assignee: UOP LLC, Des Plaines, IL (US)

( * ) Notice: Subject to any disclaimer, the term of this patent is extended or adjusted under 35 U.S.C. 154(b) by 73 days.

(21) Appl. No.: 14/193,300

(22) Filed: Feb. 28, 2014

(65) Prior Publication Data

US 2015/0247784 A1    Sep. 3, 2015

(51) Int. Cl.
*G01N 1/20* (2006.01)
*G01N 1/22* (2006.01)
*G01N 33/28* (2006.01)
*G01N 1/10* (2006.01)

(52) U.S. Cl.
CPC .......... *G01N 1/2035* (2013.01); *G01N 33/2823* (2013.01); *G01N 2001/105* (2013.01); *G01N 2001/1062* (2013.01); *G01N 2001/205* (2013.01); *G01N 2001/2064* (2013.01); *G01N 2001/2071* (2013.01); *Y10T 436/25875* (2015.01)

(58) Field of Classification Search
CPC .............. G01N 1/2035; G01N 1/2226; G01N 2001/205
USPC ........................................................ 436/180
See application file for complete search history.

(56) References Cited

U.S. PATENT DOCUMENTS

| 3,208,230 | A | 9/1965 | Fourroux |
| 3,649,202 | A | 3/1972 | Bajek et al. |
| 3,751,229 | A | 8/1973 | Bajek et al. |
| 5,277,881 | A | 1/1994 | Partridge, Jr. et al. |
| 5,347,066 | A | 9/1994 | Randolph |
| 5,583,049 | A | 12/1996 | Altman et al. |
| 6,096,553 | A | 8/2000 | Heald et al. |
| 6,387,705 | B1 | 5/2002 | Claibourn et al. |
| 6,909,269 | B2 * | 6/2005 | Nagai ................ G01N 15/1209 324/71.1 |
| 2012/0137754 | A1 | 6/2012 | Henry |
| 2013/0191036 | A1 | 7/2013 | Trygstad et al. |

FOREIGN PATENT DOCUMENTS

WO    97/49979 A1    12/1997

OTHER PUBLICATIONS

Eastman, et al., "Consider Online Monitoring of HF Acid When Optimizing Alkylation Operations," Hydrocarbon Processing, v 80, n 8, p. 95-100, Aug. 2001, ISSN: 00188190, Gulf Publishing Co.
Heald, et al., "On-Line Analysis of HF Acid Using Near-Infrared Spectroscopy," 1997 NPRA Annual Meeting, San Antonio, Texas, Mar. 16-18, ISSN 0470-200X, N. AM-97-57, Mar. 16, 1997, National Petroleum Refiners Association (NPRA).

* cited by examiner

Primary Examiner — Paul Hyun

(57) ABSTRACT

Methods, apparatuses, and kits for collecting chemical samples are provided. In one embodiment, a method for collecting a sample of a chemical from a vessel includes connecting a sampling chamber and a removal chamber in fluid communication with the vessel and flowing a liquid phase of the chemical from the vessel through the sampling chamber and the removal chamber. The method isolates a first volume of the liquid phase in the sampling chamber and removes a second volume of the liquid phase from the removal chamber. Further, the method includes establishing fluid communication between the sampling chamber and the removal chamber and filling the removal chamber with a portion of the first volume to form a vapor phase of the chemical in the sampling chamber. Also, the method includes isolating the sample including the vapor phase and a remaining portion of the liquid phase in the sampling chamber.

11 Claims, 4 Drawing Sheets

METHODS, APPARATUSES AND KITS FOR COLLECTING CHEMICAL SAMPLES

TECHNICAL FIELD

The technical field generally relates to methods, apparatuses, and kits for collecting chemical samples, and more particularly relates to methods, apparatuses, and kits for collecting chemical samples including liquid and vapor portions.

BACKGROUND

During chemical processing, it may be desirable or necessary to analyze a stream such as a feed stream, process stream, or product stream, to determine its composition and to determine whether chemical process conditions are optimal. Such process analysis typically involves collecting a sample from a selected stream in a sampling cylinder and analyzing the sample outside of the processing unit.

Analysis of certain chemicals, such as light end hydrocarbons, may require collection of a sample including a liquid portion and a vapor portion. In certain circumstances, the analytical method may require a liquid and vapor portion for accuracy. Additionally or alternatively, the analytical method may require a liquid and vapor portion for purposes of safety. For example, the vapor portion may provide a safety margin to mitigate concerns of sampling cylinder rupture caused by thermal expansion in a liquid-filled sampling cylinder.

To verify that a sample includes a liquid and vapor portion, conventional sampling cylinders are typically used with pipes or tubes having transparent windows or sight glasses. For such a conventional sampling cylinder used with pipes or tubes having transparent windows, a collected sample may be optically inspected to verify the presence of a vapor portion, such as by locating a vapor-liquid phase boundary. However, sight glasses are not appropriate for use with certain chemicals. For example, alkylation processes using hydrofluoric (HF) acid may require process analysis. Streams under analysis in such HF alkylation processes may chemically attack the sight glass used with a sampling cylinder. As a result, the sight glass may be structurally compromised and undesirable leakage of process streams may occur. To ensure safety, use of sight glasses may be completely banned around such processing units.

Accordingly, it is desirable to provide improved methods, apparatuses, and kits for collecting chemical samples. It is also desirable to provide methods, apparatuses, and kits for collecting chemical samples that ensure collection of a sample with a liquid portion and a vapor portion. Also, it is desirable to provide such methods, apparatuses, and kits for collecting chemical samples that avoid use of sight glasses or windows. Furthermore, other desirable features and characteristics will become apparent from the subsequent detailed description and the appended claims, taken in conjunction with the accompanying drawings and the foregoing technical field and background.

BRIEF SUMMARY

Methods, apparatuses, and kits for collecting chemical samples are provided. In an exemplary embodiment, a method for collecting a sample of a chemical from a vessel includes connecting a sampling chamber and a removal chamber in fluid communication with the vessel and flowing a liquid phase of the chemical from the vessel through the sampling chamber and the removal chamber. The method isolates a first volume of the liquid phase in the sampling chamber and removes a second volume of the liquid phase from the removal chamber. Further, the method includes establishing fluid communication between the sampling chamber and the removal chamber and filling the removal chamber with a portion of the first volume to form a vapor phase of the chemical in the sampling chamber. Also, the method includes isolating the sample including the vapor phase and a remaining portion of the liquid phase in the sampling chamber.

In another embodiment, an apparatus for collecting a sample of a chemical is provided. The apparatus includes a sampling chamber configured for selective connection to a vessel holding the chemical to fill the sampling chamber with the chemical. The apparatus further includes a removal chamber configured for selective connection to the sampling chamber to remove a portion of the chemical from the sampling chamber. Also, the apparatus includes a plurality of valves interconnected with the vessel, sampling chamber, and removal chamber. The plurality of valves are configured to sequentially isolate the sampling chamber, connect the sampling chamber to the removal chamber to remove the portion from the sampling chamber to provide a vapor space in the sampling chamber, and isolate the sampling chamber to collect the chemical sample including the vapor space.

In accordance with another exemplary embodiment, a kit for collecting a chemical sample from a vessel is provided. The kit includes a sampling chamber, and a first valve and a second valve configured for connection to the sampling chamber. The first valve and second valve selectively close to isolate chemical within the sampling chamber. The kit further includes a removal chamber configured for connection to the second valve and a third valve configured for connection to the removal chamber. The second valve and third valve selectively close to isolate chemical within and between the sampling chamber and the removal chamber.

BRIEF DESCRIPTION OF THE DRAWINGS

Embodiments of methods, apparatuses, and kits for collecting chemical samples will hereinafter be described in conjunction with the following drawing figures wherein.

DETAILED DESCRIPTION

The following detailed description is merely exemplary in nature and is not intended to limit the methods, apparatuses, and kits for collecting chemical samples. Furthermore, there is no intention to be bound by any theory presented in the preceding background or the following detailed description.

As described herein, methods, apparatuses, and kits are provided for collecting chemical samples. The methods, apparatuses, and kits are provided to ensure collection of a sample having a liquid portion and a vapor portion. Further, such methods, apparatuses, and kits ensure collection of a sample having a liquid portion and a vapor portion without requiring optical inspection of the sample and, thus, a sight glass or window.

Specifically, optical inspection is not required due to the physical treatment of a chemical to be sampled. In an exemplary embodiment herein, a sampling chamber is arranged in fluid communication with a removal chamber. Flow of a chemical to be collected is directed through the sampling chamber and the removal chamber. While the exemplary sampling chamber is filled with the chemical, flow in and out of the sampling chamber is suspended. The exemplary removal chamber may be drained of the chemical and a low pressure atmosphere may be established therein. In the exemplary embodiment, flow between the sampling chamber and the emptied removal chamber is reopened and, under the low pressure atmosphere of the emptied removal chamber, the chemical fills the removal chamber. As a result, a vapor space is formed in the exemplary sampling chamber. The exemplary sampling chamber is then isolated from the removal chamber, with the liquid and vapor space therein forming a sample for testing. In this manner, it can be ensured that the sampling chamber includes a vapor space, as may be required for analysis.

Figure 1:
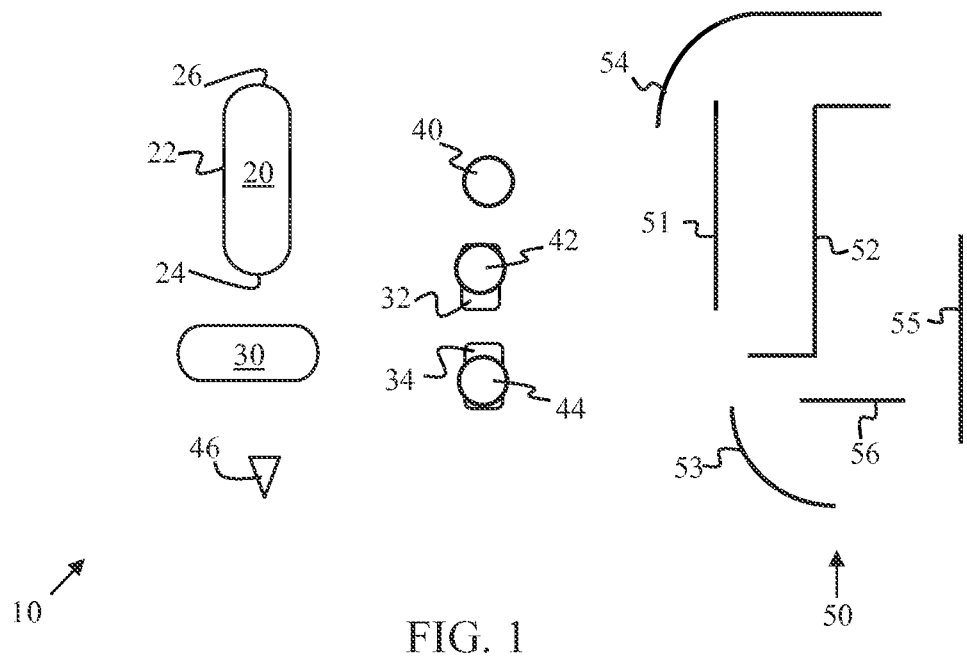
FIG. 1 is a schematic diagram of a kit for collecting chemical samples in accordance with an embodiment.

Referring to FIG. 1, an exemplary assembly 10 for collecting a chemical sample is illustrated. The exemplary assembly 10 may be provided as a kit for forming an apparatus to collect a chemical sample onsite. Further, the exemplary assembly 10 may include more than one of each illustrated component including components of different sizes or having different properties for use with selected processing. For example, the components may be formed from different materials, with the metallurgical or physical properties of the materials being designed for use in safely and effectively collecting specific chemicals.

The exemplary assembly 10 includes a sampling chamber 20. An exemplary sampling chamber 20 is formed with a cylindrical shell 22 and has an inlet 24 and an outlet 26. The exemplary sampling chamber 20 defines a sampling volume. The exemplary assembly 10 also includes a removal chamber 30. The exemplary removal chamber 30 is smaller than the sampling chamber 20 such that it defines a removal volume that is less than the sampling volume. The removal chamber 30 includes openings to receive and allow a liquid to pass through. The exemplary assembly 10 also includes two fittings 32 and 34, such as quick connect fittings as are known in the art. The exemplary fittings 32 and 34 are designed to mount and dismount from the inlet 24 and outlet 26 of the sampling chamber 20. Such quick connect fittings are well-known and may make use of a variety of structural engagements with the sampling chamber 20 to ensure leak-proof connection while providing ease in disconnection.

The exemplary assembly 10 also includes a plurality of valves. For example, the assembly 10 includes a valve 40, valve 42 and valve 44. The assembly may include more valves in certain embodiments. An exemplary valve 40 is a multiple direction valve, such as a three-way valve. In an exemplary embodiment, at least two valves, such as 40 and 42, permit flow in two directions, while one valve, such as valve 44 may be a one-way valve. Regardless of the specific valve structure, each valve is configured for selectively controlling flow of the chemical therethrough. As shown in FIG. 1, valve 42 may be provided in connection with quick connect fitting 32, and valve 44 may be provided in connection with quick connect fitting 34. Alternatively, the fittings 32 and 34 and valves 42 and 44 may be separate components.

The exemplary assembly 10 further includes a pressure gauge 46. Also, the exemplary assembly 10 includes a plurality 50 of tubes, such as tube 51, tube 52, tube 53, tube 54, tube 55 and tube 56. Each tube may be rigid or flexible, or include rigid and flexible portions. Further, each tube defines a passageway for permitting flow of chemical to be collected. Each tube is configured for connection to the inlet 24 or outlet 26 of the sampling chamber 20, the removal chamber 30, the fittings 32 and 34, the valves 40, 42 and 44, and/or the pressure gauge 46, as well as to a chemical processing vessel and exit vent. Such connection may be provided using any suitable known configuration.

Figure 2:
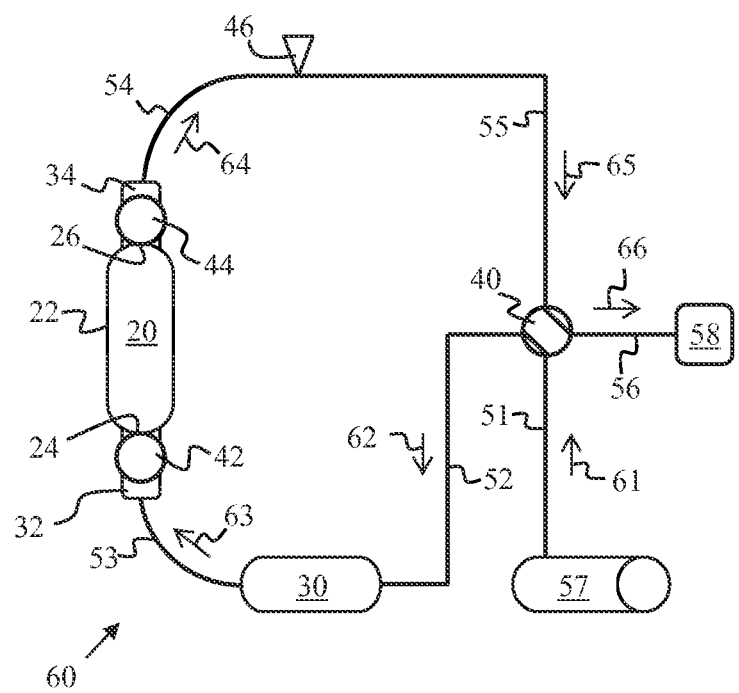
FIG. 2 is a schematic diagram of an apparatus for collecting chemical samples formed from the kit of FIG. 1 and in a first configuration for a method for collecting chemical samples in accordance with an embodiment.

In FIG. 2, the assembly 10 of FIG. 1 is connected and arranged for collection of a liquid chemical from a processing unit or vessel 57, such as a reactor or conduit and for release of excess chemical through an exit vent 58. As arranged, the assembly forms an apparatus 60. Unlike conventional apparatuses, apparatus 60 is windowless, i.e., its components are continuous and enclose a fluid path with no vantage point providing a view to the fluid path. In FIG. 2, the apparatus 60 is shown in a first configuration to collect a chemical sample. As used herein, "downstream" and "upstream" indicate a relative position based on the direction of flow from the processing unit 57 through the apparatus 60 and to the exit vent 58. However, as explained below, in embodiments flow of the chemical occurs in both the downstream and upstream directions during operation of the apparatus 60.

In a downstream direction from the processing unit 57, the apparatus 60 includes the tube 51 connected to the processing unit 57 and to the valve 40. The exemplary valve 40 is further connected to the tube 52. The tube 52 is connected in fluid communication with the removal chamber 30. The removal chamber 30 is connected in fluid communication with the tube 53 that is, in turn, connected in fluid communication with the fitting 32. In FIG. 2, the valve 42 is connected with the fitting 32. Fitting 32 is also in fluid communication with the inlet 24 of the sampling chamber 20.

The outlet 26 of the exemplary sampling chamber 20 is in fluid communication with the fitting 34. Also, valve 44 is connected with the fitting 34. Further, fitting 34 is in fluid communication with tube 54, which is connected in fluid communication with tube 55. While shown as two different tubes, tube 54 and tube 55 may be provided as a single component. As shown, pressure gauge 46 is connected to tube 54 and may measure pressure of fluid therein. Tube 55 is further connected to the valve 40, which is also connected to tube 56. Tube 56 is connected to the exit vent 58.

Referring again to FIG. 2, the exemplary valve 40 is illustrated as a three-way valve providing selective flow from tube 51 to tube 52, i.e., from the processing unit 57 to the sampling chamber 20, and from tube 55 to tube 56, i.e., from the sampling chamber 20 to the exit vent 58. However, although not shown, the assembly 10 and apparatus 60 may instead include a valve dedicated to controlling flow in from the processing unit 57 and a separate valve dedicated to controlling flow out from the sampling chamber 20 to the exit vent 58.

For use in collecting a chemical sample, the apparatus 60 may be assembled from the kit 10 as illustrated and then set in a first configuration. In the illustrated first configuration of FIG. 2, the valve 40 is opened to permit flow of the chemical from the processing unit 57 to the removal chamber 30. Also, in the first configuration, the valve 42 is opened to permit flow of the chemical from the removal chamber 30 to the sampling chamber 20. Likewise, in the first configuration, the valve 44 is opened and the valve 40 is opened to permit flow of the chemical from the sampling chamber 20 to the exit vent 58.

The apparatus 60 may be maintained in the first configuration to allow the chemical to flush or rinse the apparatus components to ensure proper sample collection. Typically, the operating pressure of the processing unit 57 is sufficient to create the flow of the chemical from the processing unit in the direction of arrows 61, 62, 63, 64, 65, and 66. After the chemical has flowed through the apparatus 60 for a desired duration of time, the apparatus 60 is manipulated to a second configuration shown in FIG. 3.

Figure 3:
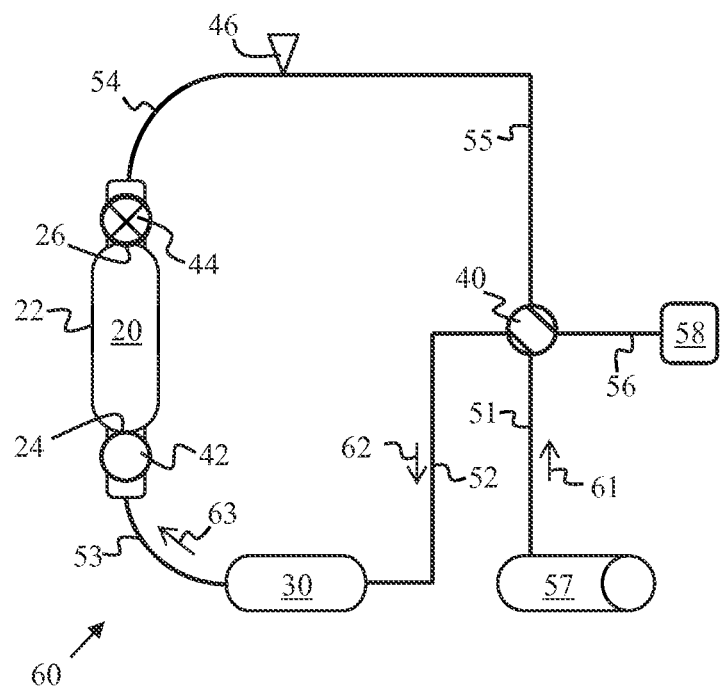
FIG. 3 is a schematic diagram of the apparatus of FIG. 2 in a second configuration for a method for collecting chemical samples in accordance with an embodiment.

In the second configuration of FIG. 3, the apparatus 60 suspends flow of the chemical therethrough. Specifically, the valve 44 is closed to stop the flow of the chemical exiting the sampling chamber 20. In the second configuration, flow of the chemical in the direction of arrows 61, 62 and 63 through the removal chamber 30 and into the apparatus 60 is slowed and then suspended as the chemical cannot exit the sampling chamber 20.

Figure 4:
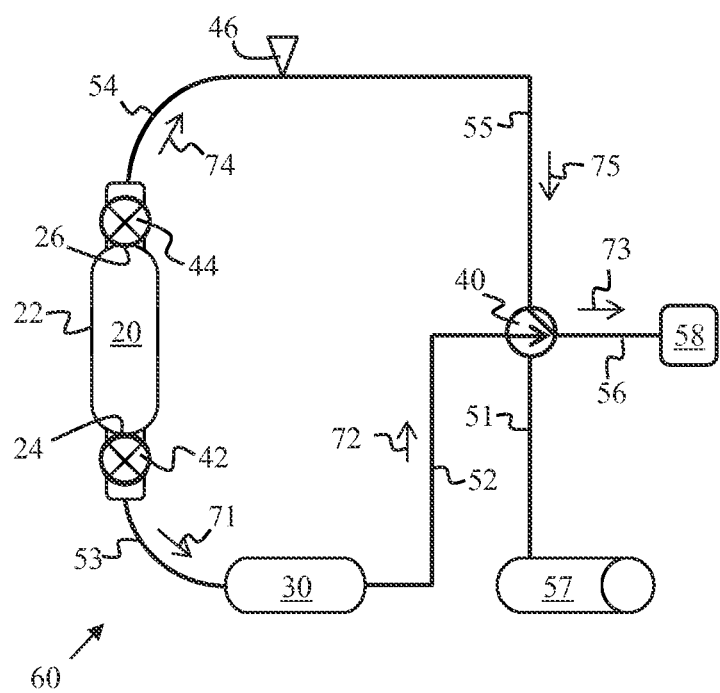
FIG. 4 is a schematic diagram of the apparatus of FIG. 2 in a third configuration for a method for collecting chemical samples in accordance with an embodiment.

In FIG. 4, the apparatus 60 is illustrated in a third configuration. In the third configuration, the valve 42 is closed, thereby trapping a volume of the chemical within the sampling chamber. The trapped volume is equal to a sampling chamber capacity. The valve 40 may be opened to flow from tube 52 to tube 56 while remaining open to flow from tube 55 to tube 56. As a result, the exit vent 58 depressurizes the apparatus 60 outside of the sampling chamber 20 and the chemical flows in the direction of arrows 71, 72 and 73 and arrows 74, 75 and 73. After the apparatus 60 is depressurized, it may be manipulated to a fourth configuration.

Figure 5:
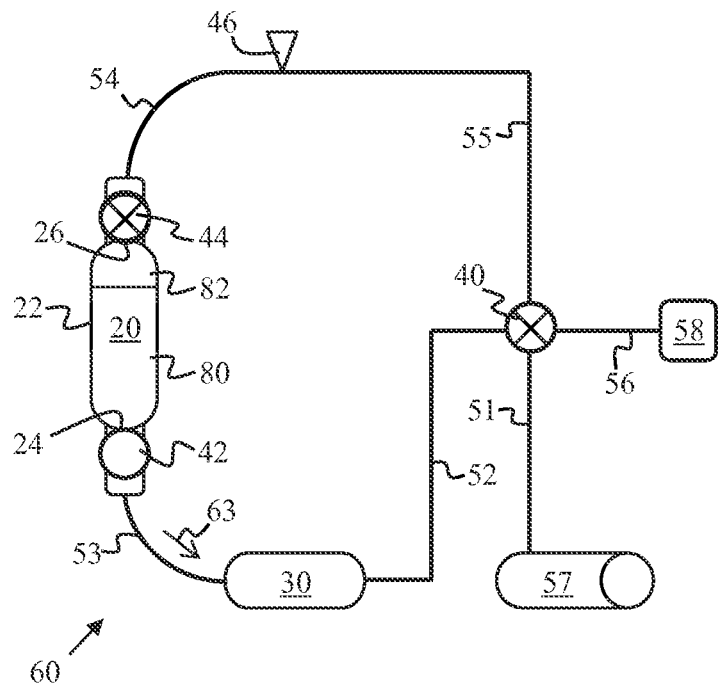
FIG. 5 is a schematic diagram of the apparatus of FIG. 2 in a fourth configuration for a method for collecting chemical samples in accordance with an embodiment.

In the fourth configuration of FIG. 5, the valve 42 between the sampling chamber 20 and the removal chamber 30 is opened, while the valves 40 and 44 remain closed. The portion of the liquid chemical within the sampling chamber 20 displaces to and fills the lower pressure removal chamber 30 by flowing in the direction of arrow 63. In other words, pressure between the sampling chamber 20 and the removal chamber 30 equalizes. In an exemplary embodiment, the portion removed from the sampling chamber 20 is substantially equal to the volume of the removal chamber 30, i.e., the removal chamber capacity, which is less than the sampling chamber capacity. As a result of the removal of the portion of the chemical from the sampling chamber 20, the pressure in the sampling chamber 20 is reduced and the liquid portion 80 of the chemical reaches equilibrium with a vapor portion 82 of the chemical. In this manner, under practical operating conditions the sampling chamber 20 is ensured to include a liquid portion 80 and vapor portion 82 of the chemical without requiring optical inspection.

Figure 6:
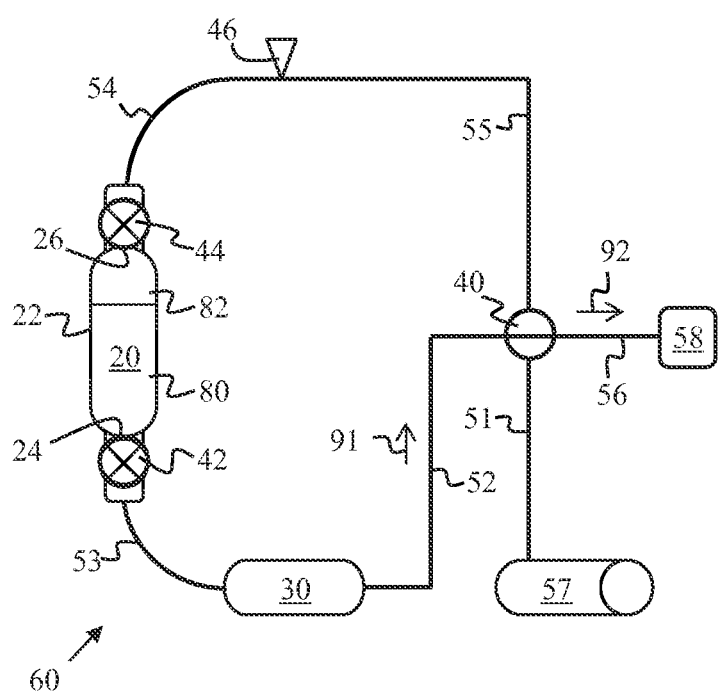
FIG. 6 is a schematic diagram of the apparatus of FIG. 2 in a fifth configuration for a method for collecting chemical samples in accordance with an embodiment.

With the liquid portion 80 and vapor portion 82 of the chemical established in the sampling chamber 20, the apparatus 60 is moved to a fifth configuration in FIG. 6 by closing the valve 42 between the sampling chamber 20 and the removal chamber 30. Further, in the fifth configuration, the valve 40 may be opened to flow between tube 53 and tube 56. As a result, the removal chamber 30 may be depressurized and the chemical upstream of the valve 42 may flow in the direction of arrows 91 and 92 to exit vent 58.

Figure 7:
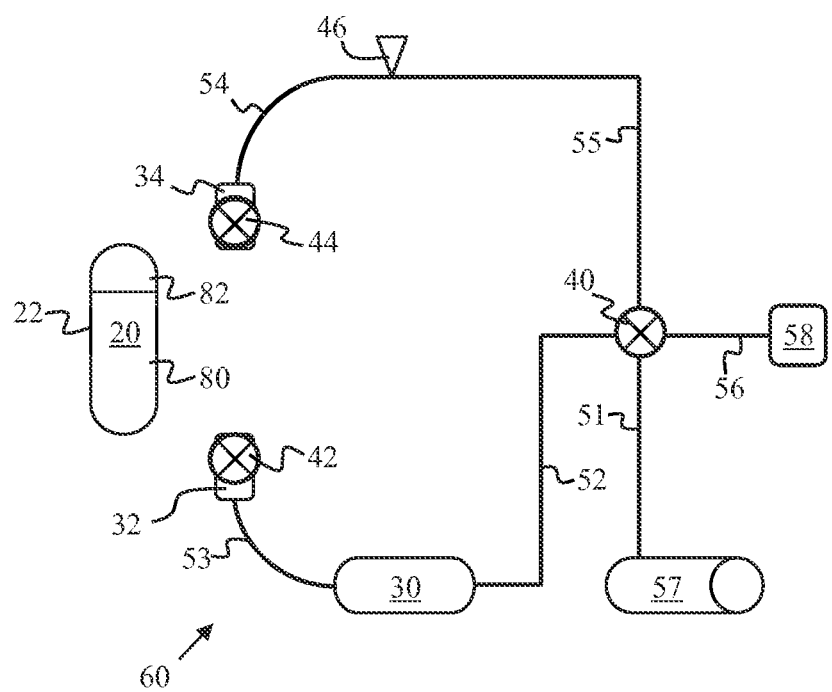
FIG. 7 is a schematic diagram of the apparatus of FIG. 2 in a sixth configuration for a method for collecting chemical samples in accordance with an embodiment.

In FIG. 7, the valve 40 may be closed in a sixth configuration of the apparatus 60. The pressure gauge 46 may be inspected to ensure that no pressure differential exists in tubes 54 and 55 downstream of the sampling chamber 20. Likewise, a pressure gauge may be provided upstream of the sampling chamber to ensure that no pressure differential exists in the removal chamber 30 and tubes 53 and 52. Alternatively, the valve 40 may be opened to provide fluid communication between tube 55 and tube 52 such that only one gauge is necessary. If an undesirable pressure exists in the apparatus 60 outside of the sampling chamber 20, the valve 40 may be opened to provide fluid communication between tube 52 and/or 55 and tube 56. When an acceptable pressure is established, the sampling chamber 20 may be disconnected from fittings 32 and 34. The sampling chamber 20 may then be transported or processed to provide the desired analysis of the chemical sample therein, including the liquid portion 80 and the vapor portion 82.

While the illustrated embodiment depicts the removal chamber 30 being positioned upstream of the sampling chamber 20 and in communication with the inlet 24 of the sampling chamber 20, it is contemplated that the removal chamber 30 be positioned downstream of the sampling chamber 20 and in communication with the outlet 26 of the sampling chamber 20. In such an embodiment, the valve 44, rather than valve 42, is opened in the fourth configuration to allow displacement of the liquid from the sampling chamber 20 to the removal chamber 30.

Further, while the exemplary embodiment of the assembly 10 and apparatus 60 include specific numbers of valves and tubes, it is noted that the embodiment is merely illustrative. The assembly 10 and apparatus 60 may include fewer or more valves and fewer or more tubes to provide selectively controlled fluid communication between the processing unit, removal chamber, sampling chamber and exit vent.

As described herein, apparatuses, assemblies and methods for collecting chemical samples have been provided. The apparatuses, assemblies and methods provide steps for collecting a chemical sample by sequentially isolating a sampling chamber, connecting the sampling chamber to a removal chamber to remove a portion of the chemical from the sampling chamber to provide a vapor space in the sampling chamber, and again isolating the sampling chamber to collect the chemical sample including the vapor space.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the claimed subject matter in any way. Rather, the foregoing detailed description will provide those skilled in the art with a convenient road map for implementing an exemplary embodiment or embodiments. It being understood that various changes may be made in the function and arrangement of elements described in an exemplary embodiment without departing from the scope set forth in the appended claims.

What is claimed is:

1. A method for collecting a sample of a chemical from a vessel, the method comprising the steps of:

connecting a sampling chamber and a removal chamber in fluid communication with the vessel;

flowing a liquid phase of the chemical from the vessel through the sampling chamber and the removal chamber;

isolating a first volume of the liquid phase of the chemical in the sampling chamber comprising isolating a first volume of the liquid phase of the chemical equal to a sampling chamber capacity;

removing a second volume of the liquid phase of the chemical from the removal chamber comprising removing a second volume of the liquid phase of the chemical equal to a removal chamber capacity, wherein the second volume is less than the first volume;

establishing fluid communication between the sampling chamber and the removal chamber and filling the removal chamber with a portion of the first volume of the liquid phase of the chemical to form a vapor phase of the chemical in the sampling chamber; and isolating the sample including the vapor phase of the chemical and a remaining portion of the liquid phase of the chemical in the sampling chamber.

2. The method of claim 1 wherein flowing the liquid phase of the chemical from the vessel through the sampling chamber and the removal chamber comprises flowing the liquid phase of the chemical in a downstream direction from the vessel through the removal chamber, and from the removal chamber through the sampling chamber, and wherein filling the removal chamber with a portion of the first volume of the liquid phase of the chemical comprises flowing the portion of the first volume of the liquid phase of the chemical in an upstream direction from the sampling chamber to the removal chamber.

3. The method of claim 1 wherein:

connecting a sampling chamber and a removal chamber in fluid communication with the vessel comprises interconnecting valves with the vessel, the sampling chamber, and the removal chamber;

flowing a liquid phase of the chemical from the vessel through the sampling chamber and the removal chamber comprises manipulating the valves to sequentially open flow of the liquid phase of the chemical in a downstream direction through the removal chamber and through the sampling chamber;

isolating a first volume of the liquid phase of the chemical in the sampling chamber comprises manipulating the valves to close flow of the liquid phase of the chemical out of and into the sampling chamber;

removing a second volume of the liquid phase of the chemical from the removal chamber comprises manipulating the valves to open flow of the second volume of the liquid phase of the chemical out of the removal chamber in an upstream direction to an exit vent;

establishing fluid communication between the sampling chamber and the removal chamber and filling the removal chamber with a portion of the first volume of the liquid phase of the chemical to form a vapor phase of the chemical in the sampling chamber comprises manipulating the valves to sequentially close flow of the liquid phase of the chemical upstream of the removal chamber and to open flow the liquid phase of the chemical between the sampling chamber and the removal chamber; and isolating the sample including the vapor phase of the chemical and a remaining portion of the liquid phase of the chemical in the sampling chamber comprises manipulating the valves to close flow of the liquid phase of the chemical out of and into the sampling chamber.

4. The method of claim 1 wherein connecting a sampling chamber and a removal chamber in fluid communication with the vessel comprises connecting a multiple direction valve between the vessel, the removal chamber, and an exit vent, and wherein removing a second volume of the liquid phase of the chemical from the removal chamber comprises flowing the second volume of the liquid phase of the chemical through the multiple direction valve to the exit vent.

5. The method of claim 1 wherein connecting a sampling chamber and a removal chamber in fluid communication with the vessel comprises interconnecting a multiple direction valve between the vessel and the removal chamber to selectively control flow of the chemical from the vessel in a downstream direction, an upstream valve upstream of the sampling chamber to selectively control flow of the liquid phase of the chemical into the sampling chamber in the downstream direction and out of the sampling chamber in an upstream direction, and a downstream valve downstream of the sampling chamber to selectively control flow of the liquid phase of the chemical out of the sampling chamber in the downstream direction.

6. The method of claim 5 wherein flowing a liquid phase of the chemical from the vessel through the sampling chamber and the removal chamber comprises opening the multiple direction valve to flow from the vessel, opening the upstream valve and opening the downstream valve.

7. The method of claim 6 wherein isolating a first volume of the liquid phase of the chemical in the sampling chamber comprises sequentially closing the downstream valve and closing the upstream valve.

8. The method of claim 7 wherein removing a second volume of the liquid phase of the chemical from the removal chamber comprises opening the multiple direction valve to flow from the removal chamber to an exit vent.

9. The method of claim 8 wherein establishing fluid communication between the sampling chamber and the removal chamber and filling the removal chamber with a portion of the first volume of the liquid phase of the chemical to form a vapor phase of the chemical in the sampling chamber comprises sequentially closing the multiple direction valve to flow from the removal chamber and opening the upstream valve to permit flow from the sampling chamber to the removal chamber.

10. The method of claim 9 wherein isolating the sample including the vapor phase of the chemical and a remaining portion of the liquid phase of the chemical in the sampling chamber comprises closing the upstream valve.

11. The method of claim 1 wherein removing a second volume of the liquid phase of the chemical from the removal chamber comprises reducing a pressure in the removal chamber, and wherein establishing fluid communication between the sampling chamber and the removal chamber comprises equalizing pressure between the sampling chamber and the removal chamber.

* * * * *